United States Patent [19]

deRuiter

[11] Patent Number: Plant 7,572

[45] Date of Patent: Jul. 2, 1991

[54] MINIATURE ROSE PLANT NAMED RUIGERDAN

[75] Inventor: Gijsbert deRuiter, Hazerswoude, Netherlands

[73] Assignee: DeRuiter's Nieuwe Rozen B.V., Netherlands

[21] Appl. No.: 479,602

[22] Filed: Feb. 12, 1990

[51] Int. Cl.[5] ..... A01H 5/00

[52] U.S. Cl. ..... Plt./10

[58] Field of Search ..... Plt. 10

*Primary Examiner*—James R. Feyrer

*Attorney, Agent, or Firm*—Christie, Parker & Hale

[57] ABSTRACT

A new variety of miniature rose having red flowers produced in sprays on a plant suitable for flower forcing and also for growing outdoor in gardens.

2 Drawing Sheets

SUMMARY OF THE INVENTION

The present invention relates to a new and distinct variety of rose plant of the miniature rose class, which was originated by my crossing as seed parent an unnamed, unpatented seedling of my creation and as pollen parent the variety known as "Amruda." The varietal denomination of this new rose is "Ruigerdan."

Among the novel characteristics possessed by this new variety which distinguish it from its parents and all other varieties of which I am aware are its attractive red flowers and floral habit whereby the flowers are produced in sprays borne on a plant suited for production of cut flower sprays. "Ruigerdan" is also suitable for growing in outdoor gardens. The new variety can be reproduced through propagation by cuttings, grafting and budding. Flowers of the new variety are long lasting after cutting. Asexual reproduction by budding and grafting of the new variety as performed in Hazerswoude, Holland, shows that the foregoing and other distinguishing characteristics come true to form and are established and transmitted through succeeding propagation.

The accompanying drawings show typical specimens of the vegetative growth and flowers of the new variety in different stages of development and depicted in color as nearly true as it is reasonably possible to make the same in color illustration of this character.

BRIEF DESCRIPTION OF THE DRAWINGS

One photo illustration shows details of the new miniature rose variety depicting flower substantially true flower color and the other photo illustration shows the floral habit of the new variety but with somewhat variant flower coloring.

DESCRIPTION OF THE PREFERRED EMBODIMENT

The following is a detailed description of my new variety, with color terminology in accordance with The Royal Horticultural Society Colour Chart (R.H.S.C.C.) and horticultural terminology in accordance with standard terminology used in UPOV-approved horticultural guidelines. The terminology used in color description herein refers to plate numbers in the aforementioned color chart.

Parentage:

*Seed parent.*—Unnamed seedling.

*Pollen parent.*—"Amruda."

Class: Miniature.

In the detail illustration there is shown the top of a young shoot 1; compount three, five and seven leaflet leaves 2, 3, and 4, respectively; a stem 5; a flower bud 6 showing color; a flower bud 7 after sepals separate further; a flower 8 about one-third to one-half open; and a flower 9 fully open. Also shown are flower stems 10, 11 and 12 displaying reproductive organs.

The following further horticultural observations were made of specimens grown under glass in Holland.

FLOWER

Blooming habit: Nearly continuous, very floriferous, early blooming.

A. Bud:

(1) *Size.*—Medium.

(2) *Form.*—Ovate.

(3) *Color.*—As sepals divide, bud color is near 46A to 46B.

(4) *Sepals.*—Longer than bud, simple to foliated.

(5) *Peduncle.*—Length — about 5 to 6 cm. Aspect — straight. Strength — erect. Color — medium green.

B. Bloom:

(1) *Flower.*—Viewed from top — irregularly rounded; Viewed from side, (A) upper part of fully opened flower — flattened convex, (B) lower part of fully opened flower — convex.

(2) *Size.*—Average size when fully expanded — about 6 cm.

(3) *Borne.*—Large sprays.

(4) *Form.*—Ovoid to cupped at first, becoming flat; Outer petals reflex to points; Inner petals roll under slightly.

(5) *Petalage.*—Number of petals under normal conditions — about 18 to 24, double.

(6) *Color.*—After sepals separate, bud coloring is near 46A to B; When sepals part and petals begin to unfurl, predominant color is near 46B; Color range of 46A to C may be evident viewing petals' top surface in ⅓ to ½ open stage; Color through this range is substantially stable. Petal top and reverse are of similar coloring. Coloring at point of petal attachment is near 7C. Overall tonality from a distance is an attractive red.

C. Petals:

(1) *Texture.*—Medium to thick.

(2) *Appearance.*—Inside velvety and outside satiny.
(3) *Form.*—Broad elliptic, little or no undulation at margin.
(4) *Arrangement.*—Regularly arranged, imbricated.
(5) *Petaloids in center.*—Few.
(6) *Persistence.*—Drop off cleanly.
(7) *Fragrance.*—Slight to none.
(8) *Lasting quality.*—Very long lasting as cut flower.

REPRODUCTIVE ORGANS

A. Stamens, filaments and anthers:
*Arrangement.*—Regularly arranged around styles.
*Color.*—Filaments deep yellow to yellow-red.
B. Pollen:
*Color.*—Yellow.
C. Styles: Even, long, stigma well above mouth of receptacle, red, upper half little to no hair, bunched.
D. Stigma: Full, extend above anthers.
E. Hips: Medium for miniature, pitcher-shaped.

PLANT

A. Form: Upright to bushy.
B. Growth: Vigorous.
*Height attained.*—About 20 to 30 cm.
C. Foliage: Compound 3, 5 and 7 leaflets.
(1) *Size.*—Medium for a miniature.
(2) *Quantity.*—Abundant.
(3) *Color.*—Foliage at time of first flowering — dark green.
(4) *Shape.*—Oval, pointed.
(5) *Texture.*—Upper side is semi-glossy; Under side is matte.
(6) *Edge.*—Serrate.
(7) *Serration.*—Ordinary, acuminate apices.
(8) *Color — medium green.*
(9) *Stipules.*—Medium length, slightly bearded, medium to light green, distinct auricle.
(10) *Leaflet.*—Cross-section — slight concave; Terminal leaflet — very short; Maximum width — very narrow; rounded base; Petiole length — short; Undulation of margin — absent or very weak.
(11) *Pedicel.*—Medium number of hairs or prickles.
D. Wood:
(1) *New wood.*—Color — bronze, purple; Young shoot — weak antocyanin coloration.
(2) *Old wood.*—Color — medium green. Bark — smooth.
E. Prickles (thorns): Present.
*Quantity (main stalk).*—Ordinary.
*On laterals from stalk.*—Few.
*Form.*—Straight and slanted slightly downward.
*Shape of upper side.*—Flat.
*Shape of lower side.*—Concave.
*Length.*—Few $\leqq 5$ mm; Medium $> 5$ mm.
*Color.*—Pink to light red.
*Position.*—Irregular.
F. Winter hardiness: Needs protection outdoors in severe climates.

I claim:

1. A new and distinct variety of rose plant of the miniature rose class, substantially as shown and described, characterized particularly by attractive red flowers which are long lasting after cutting borne on a plant suitable for producing cut flower sprays and for growing outdoor in gardens.

* * * * *

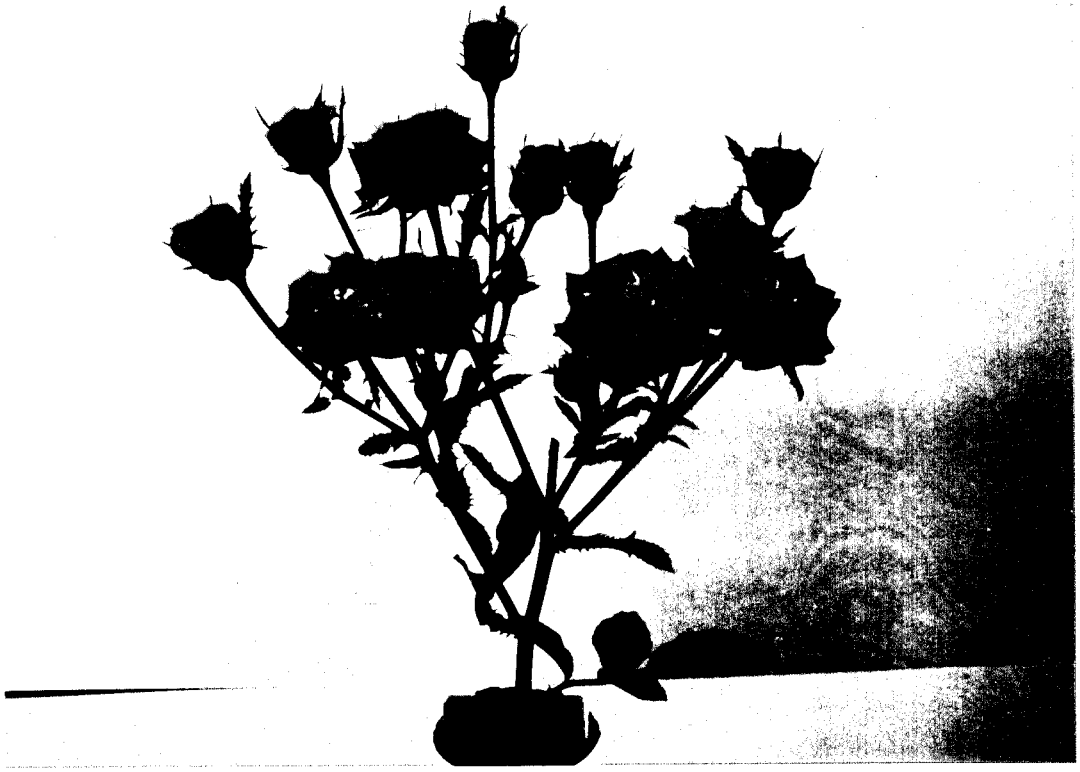

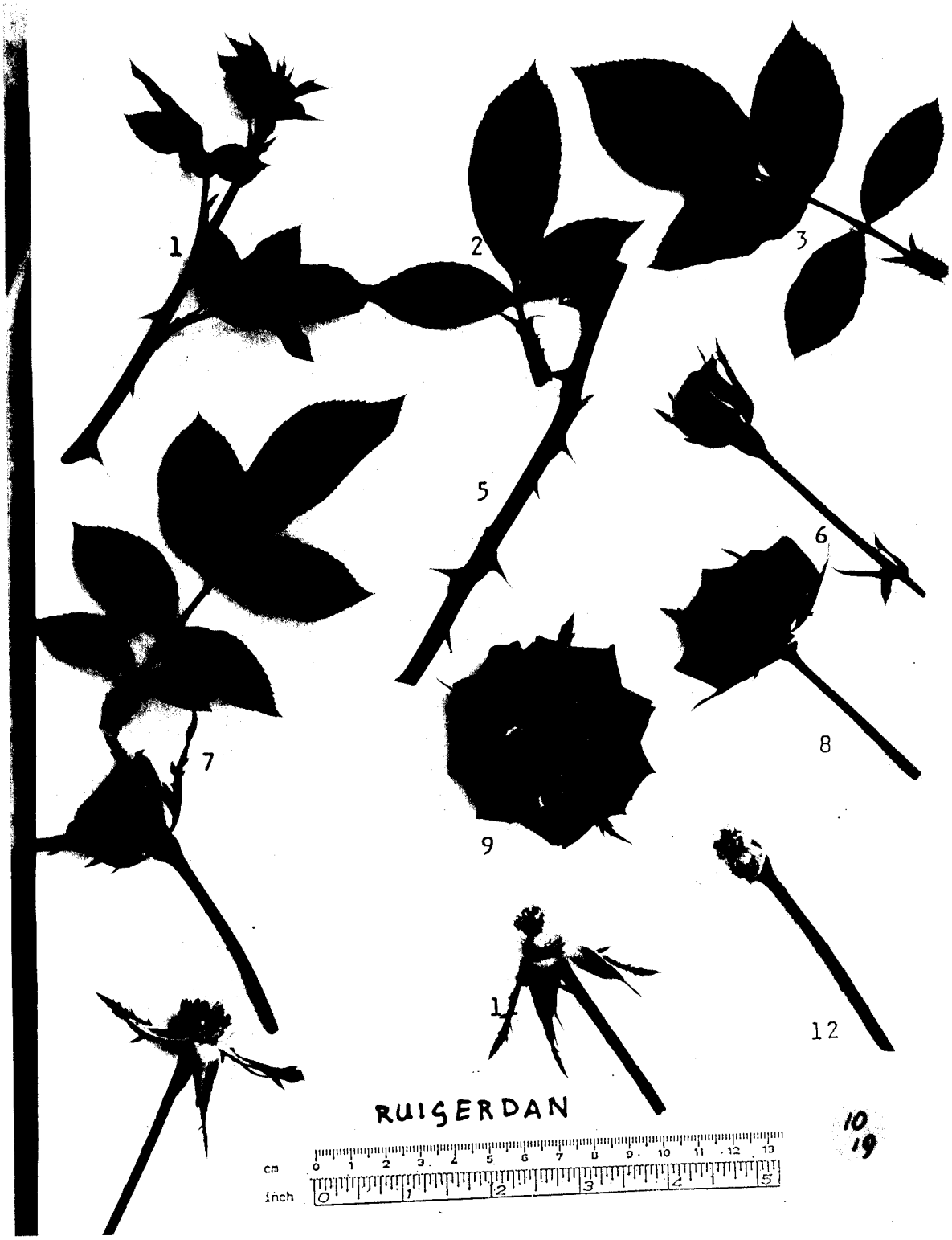
1
2
3
5
6
7
8
9
11
12
RUIGERDAN
cm
inch
10
19

UNITED STATES PATENT AND TRADEMARK OFFICE

CERTIFICATE OF CORRECTION

PATENT NO. : Plant 7,572

DATED : July 2, 1991

INVENTOR(S) : Gijsbert de Ruiter

It is certified that error appears in the above-identified patent and that said Letters Patent is hereby corrected as shown below:

Column 2, line 13, before "FLOWER" insert -- 1. --.

Column 3, line 11, before "REPRODUCTIVE ORGANS" insert -- 2. --.

Column 3, line 23, before "PLANT" insert -- 3. --.

Column 4, line 2, before "Color" insert -- Leaf Stem: --.

Column 4, line 13, change "antocyanin" to -- anthocyanin --.

Signed and Sealed this

Twenty-third Day of November, 1993

*Attest:*

*Attesting Officer*

Bruce Lehman

BRUCE LEHMAN

*Commissioner of Patents and Trademarks*